United States Patent
Hunziker et al.

(10) Patent No.: US 8,585,618 B2
(45) Date of Patent: Nov. 19, 2013

(54) BROAD-AREA IRRADIATION OF SMALL NEAR-FIELD TARGETS USING ULTRASOUND

(75) Inventors: Lukas Hunziker, Brisbane, CA (US); Justin May, Redwood City, CA (US); Tonee Smith, Redwood City, CA (US)

(73) Assignee: Cutera, Inc., Brisbane, CA (US)

( * ) Notice: Subject to any disclaimer, the term of this patent is extended or adjusted under 35 U.S.C. 154(b) by 446 days.

(21) Appl. No.: 12/642,686

(22) Filed: Dec. 18, 2009

(65) Prior Publication Data

US 2010/0160837 A1    Jun. 24, 2010

Related U.S. Application Data

(60) Provisional application No. 61/139,813, filed on Dec. 22, 2008.

(51) Int. Cl.
*A61N 7/02* (2006.01)

(52) U.S. Cl.
USPC .................................. 601/2; 601/3

(58) Field of Classification Search
USPC ........................................... 601/2, 3
See application file for complete search history.

(56) References Cited

U.S. PATENT DOCUMENTS

| | | | |
|---|---|---|---|
| 4,460,841 A * | 7/1984 | Smith et al. ................... 310/334 |
| 5,143,063 A | 9/1992 | Fellner | |
| 5,187,981 A * | 2/1993 | Chen et al. ...................... 73/642 |
| 5,346,499 A | 9/1994 | Garenfeld et al. | |
| 5,460,595 A | 10/1995 | Hall et al. | |
| 5,522,814 A | 6/1996 | Bernaz | |
| 5,558,623 A * | 9/1996 | Cody ................................ 601/2 |
| 5,669,916 A | 9/1997 | Anderson | |
| 5,989,267 A | 11/1999 | Anderson | |
| 6,113,559 A | 9/2000 | Klopotek | |
| 6,200,326 B1 | 3/2001 | Narayanan et al. | |
| 6,325,769 B1 | 12/2001 | Klopotek | |
| 6,419,648 B1 * | 7/2002 | Vitek et al. ....................... 601/3 |
| 6,500,141 B1 | 12/2002 | Irion et al. | |
| 6,544,259 B1 | 4/2003 | Tsaliovich | |

(Continued)

FOREIGN PATENT DOCUMENTS

DE    10140064 A1    3/2003
WO    WO-98/32379 A1    7/1998

(Continued)

OTHER PUBLICATIONS

Bickmore, H.R. (2004). *Milady's Hair Removal Techniques: A Comprehensive Manual*. Thomson Delmar Learning.

(Continued)

*Primary Examiner* — Unsu Jung
*Assistant Examiner* — Rajeev Siripurapu
(74) *Attorney, Agent, or Firm* — Morrison & Foerster LLP

(57) ABSTRACT

An ultrasonic transducer system for treating a portion of tissue. The ultrasonic transducer system includes a frequency generator, an ultrasonic transducer, and a transmitter element. The transducer receives an AC voltage from the frequency generator and produces an ultrasonic energy pulse at an ultrasonic frequency for a pulse width. The transmitter element is coupled to the transducer and is for irradiating a portion of skin tissue. The transmitter element has a chilled surface in contact with the skin tissue and an acoustic aperture for producing a substantially collimated energy beam. The beam has a width greater than 4 mm.

9 Claims, 18 Drawing Sheets

(56) References Cited

U.S. PATENT DOCUMENTS

| | | |
|---|---|---|
| 6,936,046 B2 | 8/2005 | Hissong et al. |
| 7,258,674 B2 | 8/2007 | Cribbs et al. |
| 2002/0055639 A1 | 5/2002 | Nebel et al. |
| 2002/0068869 A1* | 6/2002 | Brisken et al. ............... 600/439 |
| 2003/0229331 A1* | 12/2003 | Brisken et al. ............... 604/500 |
| 2004/0171970 A1 | 9/2004 | Schleuniger et al. |
| 2004/0260214 A1* | 12/2004 | Echt et al. ...................... 601/46 |
| 2005/0043726 A1* | 2/2005 | McHale et al. ................. 606/27 |
| 2005/0143677 A1 | 6/2005 | Young et al. |
| 2005/0154332 A1 | 7/2005 | Zanelli et al. |
| 2006/0074313 A1 | 4/2006 | Slayton et al. |
| 2006/0074355 A1* | 4/2006 | Slayton et al. ................... 601/2 |
| 2006/0084891 A1 | 4/2006 | Barthe et al. |
| 2006/0086604 A1* | 4/2006 | Puskas ...................... 204/157.15 |
| 2007/0016117 A1 | 1/2007 | Sliwa et al. |
| 2007/0038156 A1 | 2/2007 | Rosenberg |
| 2007/0078290 A1 | 4/2007 | Esenaliev |
| 2007/0173746 A1 | 7/2007 | Barzilay et al. |
| 2007/0239079 A1 | 10/2007 | Manstein et al. |
| 2008/0139974 A1 | 6/2008 | Da Silva |
| 2008/0154157 A1 | 6/2008 | Altshuler et al. |
| 2008/0183110 A1 | 7/2008 | Davenport et al. |
| 2008/0214988 A1* | 9/2008 | Altshuler et al. ................ 604/21 |
| 2009/0116800 A1* | 5/2009 | DiGiovanni et al. ......... 385/124 |

FOREIGN PATENT DOCUMENTS

| | | |
|---|---|---|
| WO | WO-00/21612 A1 | 4/2000 |
| WO | WO-01/13757 A1 | 3/2001 |
| WO | WO-01/26735 A1 | 4/2001 |
| WO | WO-01/33991 A1 | 5/2001 |
| WO | WO-02/09813 A1 | 2/2002 |
| WO | WO-02/092168 A1 | 11/2002 |
| WO | WO-2005/079687 A2 | 9/2005 |
| WO | WO-2007/118229 A2 | 10/2007 |
| WO | WO-2008/070580 A3 | 6/2008 |
| WO | WO-2008/074005 A1 | 6/2008 |
| WO | WO-2008/091625 A2 | 7/2008 |

OTHER PUBLICATIONS

Edmonds, P.D. et al. (1985). "Spatial Distributions of Heating by Ultrasound Transducers in Clinical Use, Indicated in a Tissue-Equivalent Phantom," *1985 Ultrasonics Symposium* pp. 908-912.

Hand, J.W. (1997). "Chapter 8: Ultrasound Hypothermia and the Prediction of Heating," *Ultrasound in Medicine*. Duck, F.A. et al (eds.). Institute of Physics Publishing.

Hill, C.R. et al. (eds.) (2004). *Physical Principles of Medical Ultrasonics*. Second Edition.John Wiley and Sons, Ltd.

\* cited by examiner

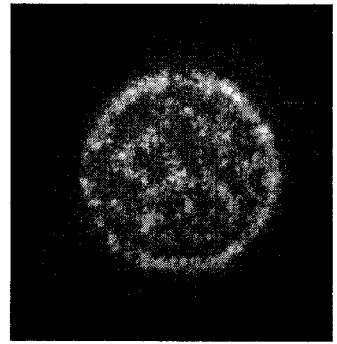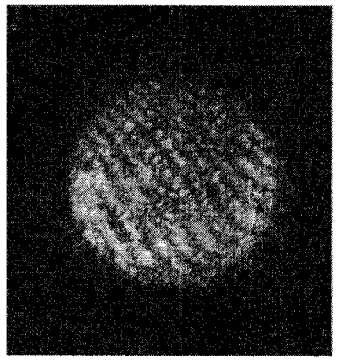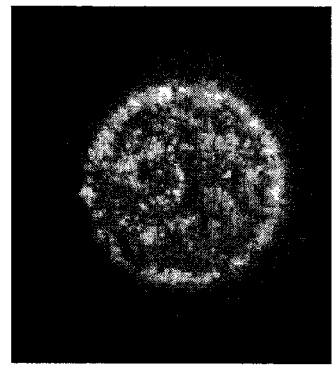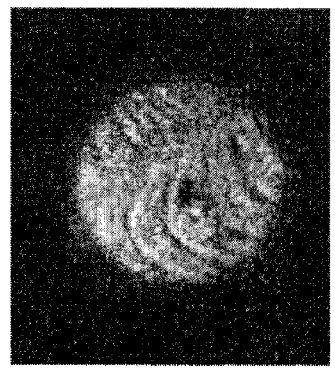
Fig. 13a
Fig. 13b

BROAD-AREA IRRADIATION OF SMALL NEAR-FIELD TARGETS USING ULTRASOUND

CROSS-REFERENCE TO RELATED APPLICATION

This application claims priority to U.S. Provisional Application Ser. No. 61/139,813 filed Dec. 22, 2008, which is incorporated herein by reference in its entirety for all purposes.

FIELD OF THE INVENTION

This application generally relates to broad-area irradiation of small targets within an irradiation area. More specifically, this application relates to the use of ultrasound irradiation to inhibit hair growth in skin tissue.

BACKGROUND

Ultrasound systems have a wide range of applications including, for example, medical procedures for imaging, diagnosis, or treatment of a human body. Using an ultrasonic transducer, energy can be transmitted to adjacent tissue so that the energy can be absorbed by parts of the body.

The concept of using ultrasound radiation to remove unwanted hair appeared in the literature as early as 1998. (Iger et al., WO 00/21612 "A Method and Device for Hair Removal," "Iger" hereinafter.) The underlying principal is to use ultrasound radiation to selectively induce damage to the hair structure and thereby retard its ability to regenerate. Typically, the bulb or bulge of the hair follicle is targeted since these features are thought to be involved in the regenerative process of hair growth. These features are commonly located several millimeters below the skin surface.

To date, two main techniques have been proposed for delivering the radiation to the hair follicle. In one, the hair shaft is gripped above the skin by some mechanical means and radiation is then coupled directly into either the side or end of the hair shaft. (See, e.g., Barzilay et al., U.S. Patent Application 2007/0173746 "Method and Device for Removing Hair," "Barzilay" hereinafter.) An ultrasonic transducer then focuses the radiation into the shaft, which transmits the energy to the hair follicle below. Alternatively, the radiation may be focused through the skin to a point of high intensity on a hair follicle. (See, e.g., Masotti., WO 02/09813 "Method and Device for Epilation by Ultrasound," "Masotti" hereinafter.) Since the targeted location is typically several millimeters below the skin surface, the practical limits of beam focusing requires that the beam radius on the skin surface to be less than several millimeters wide.

These beam delivery methods are similar in that they both use a form of spatial selectivity to concentrate the radiation within the hair structure, and thereby damage it, without affecting the surrounding tissues. In addition, both techniques focus the beam onto the hair to generate the intensity required to create damage. Two advantages of this approach are: 1) the target is located in the far-field of the transducer (close to the focal plane) where the beam's intensity profile has a smooth shape; 2) a low-power transducer is required since the output intensity at the transducer is significantly lower before it is focused. However, the inherent spatial selectivity prevents the application of these techniques to treating many hairs simultaneously. In particular, the wide variability in the spacing, angle, and length of hair shafts makes it impractical to grab, position, and efficiently irradiate a large number of hairs at one time. Because the spacing of the hairs may vary slightly, it is also impractical to design a device with multiple focal points aligned to individual follicles.

This lack of scalability makes these techniques unsuitable alternatives to existing light-based technologies that are capable of treating large areas in a short period of time. For example, common areas for light-based hair removal treatments include the axilla (armpit), arms, legs, back, chin, and pubic areas where the hair density ranges from 50 to 500 follicles/cm$^2$. (Helen R. Bickmore, *Milady's Hair Removal Techniques: A Comprehensive Manual*, Thompson Learning Inc. (2004).) Using light-based technologies, the typical treatment area may range from 1 to more than 100 cm$^2$, and the treatments can be performed at speeds up to 3 cm$^2$/sec. As a result, using light-based technologies, 50 to 50,000 hairs may be treated in a period between 1 and 33 sec.

What's needed is an ultrasonic device that can deliver performance comparable to existing light-based techniques. Specifically, there is a need for an ultrasonic device that can treat multiple hairs using a wide-area exposure. Preferably, a device should have an effective treatment area of about 1 mm$^2$ or greater since this would allow treatment of at least 5 hairs at one time.

SUMMARY

In one aspect of the present invention, an ultrasonic transducer system for treating tissue comprises: a frequency generator, a transducer, and a transmitter element. The frequency generator generates an AC voltage. The transducer receives the AC voltage from the frequency generator and produces an ultrasonic energy pulse at an ultrasonic frequency for a pulse width. The transmitter element is coupled to the transducer and irradiates a portion of skin tissue. The transmitter element has a chilled surface in contact with the skin tissue. The transducer or transmitter has an acoustic aperture for producing a substantially collimated energy beam. The substantially collimated energy beam has a width greater than 4 mm.

In some aspects, the transmitter element is comprised of at least one layer with a thickness and an acoustic impedance. The thickness and acoustic impedance of the transmitter element are selected so that at least 50% of the ultrasonic energy pulse is transmitted into the skin tissue.

In some aspects, the ultrasonic energy pulse has an acoustic wavelength, and the square of half the acoustic aperture, divided by the product of the acoustic wavelength and the distance from the acoustic aperture to 5 mm below the skin surface, is greater than 10.

In some aspects, the intensity of the ultrasonic energy pulse is greater than or equal to 150 W/cm, the ultrasonic frequency is between 5 and 20 MHz, and the pulse width is less than 100 milliseconds.

In some aspects, the acoustic aperture has a non-circular shape. In some aspects, the acoustic aperture may have a quadrilateral shape or an elliptical shape. In some aspects, the acoustic aperture has a rounded shape with one of a serrated, rippled, notched, or jagged edge profile.

In some aspects, the transmitter element includes an apodizing annulus for attenuating the transmitted power near the perimeter of the energy beam. The intensity of the transmitted power near the perimeter of the energy beam is within 20% of the intensity of the transmitted power near the center of the energy beam.

Some aspects of the present invention include a method of inhibiting hair growth in a skin tissue. The method includes placing an ultrasonic transducer in contact with the skin tissue. The transducer has an acoustic aperture for producing a substantially collimated energy beam over a treatment area greater than 16 mm². The transducer also has a chilled surface in contact with the skin tissue. The tissue has a plurality of hair follicles within the treatment area. The method further includes generating one or more ultrasonic energy pulses, each energy pulse at a corresponding frequency and pulse width.

DESCRIPTION OF THE FIGURES

FIG. 13a depicts a comparison of calculated and measured intensity profiles using two frequencies with 2:1 weighting.

FIG. 13b depicts a comparison of calculated and measured intensity profiles using six frequencies with 1:1:2:7:4:3 weighting.

Figure 1:
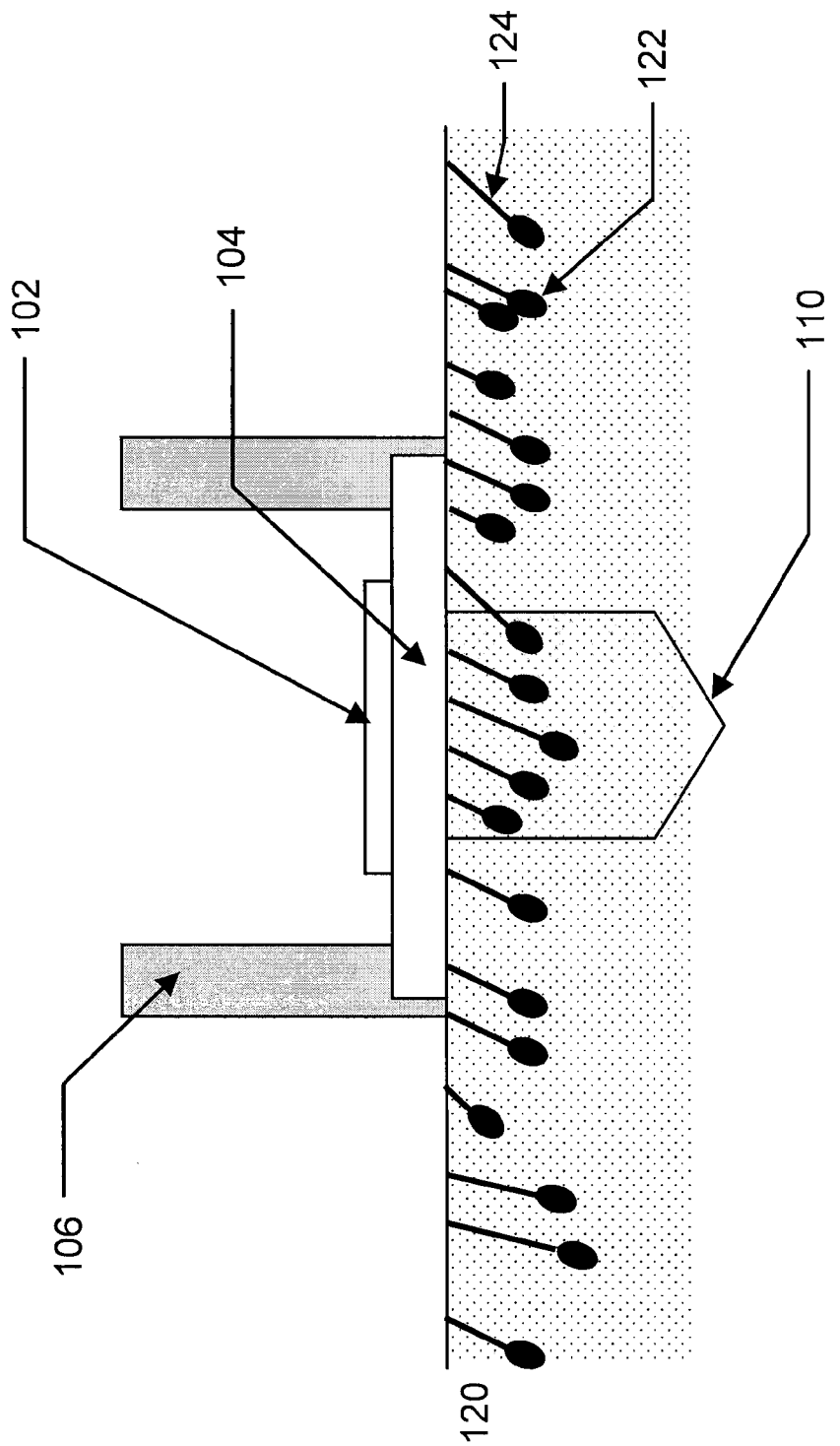
FIG. 1 depicts an embodiment of a transducer with an impedance-matching chill plate.

The figures depict one embodiment of the present invention for purposes of illustration only. One skilled in the art will readily recognize from the following discussion that alternative embodiments of the structures and methods illustrated herein can be employed without departing from the principles of the invention described herein.

DETAILED DESCRIPTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

In some embodiments, an ultrasonic transducer is used to treat to a portion of tissue. In the field of dermatology, skin tissue may be treated using irradiation produced by an ultrasonic transducer placed in contact with the surface of the skin. An ultrasonic transducer is useful for performing a variety of treatments including, for example, skin laxity, skin wrinkles, and skin hair removal. In a preferred embodiment, skin hair may be treated using an ultrasonic transducer. In the case of hair reduction by ultrasound, the goal is to damage the hair follicle by ultrasound-induced thermal or mechanical effects In general, an ultrasonic device may be characterized as a device capable of producing displacements at a frequency higher than the audible range of a human ear (frequencies>20, 000). Ultrasonic devices typically include a transducer that converts electrical energy into acoustical energy via vibrational motion at ultrasonic frequencies. The ultrasonic vibration is induced by exciting one or more piezoelectric ("piezo") elements of the transducer using an electrical signal. In a preferred embodiment, a high-frequency electrical signal is transmitted to a pair of electrodes coupled to one or more piezoelectric elements, whereby an electric field is established across the one or more piezoelectric elements. The electric field generates a mechanical standing wave at a frequency approximately equal to the frequency of the electrical signal. The mechanical standing wave is able to transmit acoustic energy through a medium. In a preferred embodiment, the piezo is mechanically coupled to a transmitter mass designed transmit the acoustic energy to a portion of the body.

1. Broad-Area Ultrasonic Transducer Device

To facilitate treatment, an ultrasonic transducer may have an applicator surface which is placed in contact with a portion of the body, herein referred to as "tissue." In one embodiment, the transducer produces a broad, unfocused (or weakly focused) beam onto an area of skin tissue such that many hairs are within the beam cross-section and may be irradiated. In contrast to the focused beam approach discussed above, the area of the broad beam remains roughly constant as the beam propagates from the skin surface to the depth of a hair follicle (up to 7 mm). Within the broad beam there is no spatial selectivity allowing the device to treat multiple hairs at a time. Also, the intensity of the radiation is nominally the same at the hair follicle as it is in the intervening tissues. Instead of the spatial selectivity of previous ultrasonic methods, a broad-area beam achieves selectivity by leveraging the stronger ultrasound absorption of hair follicles compared to the surrounding soft tissues.

A goal of a preferred embodiment is to optimize the amount of energy absorbed by the hair follicle without damaging surrounding tissue. The energy absorbed in the hair follicle induces a temperature rise in the bulb or bulge of the follicle, which is believed to provide an effective treatment for hair removal.

In preferred embodiments, a device uses beam frequencies between 5 and 20 MHz. In a more preferred embodiment, a device uses beam frequencies between 7 and 15 MHz. In preferred embodiments, a device uses pulse durations between 5 and 100 ms. In a more preferable embodiment, the pulse duration is between 5 and 75 ms. In the most preferable embodiment, the pulse duration is between 5 and 50 ms. In preferred embodiments, the beam area is greater than or equal to 4 mm². In a more preferable embodiment, the beam area is greater than or equal to 16 mm². In the most preferable embodiment, the beam area is greater than or equal to 50 mm². In preferred embodiments, the beam intensity is greater than or equal to 150 W/cm². In a more preferable embodiment, the beam intensity is greater than or equal to 300 W/cm².

In some embodiments, the ultrasonic transducer is used in a single pulse "stamping mode." For example, the ultrasonic transducer may be placed at a first location covering a first area of tissue. The transducer irradiates the first area of tissue with an ultrasonic pulse. The transducer may then be placed at a second location covering a second area of tissue. The transducer irradiates the second area of tissue with an ultrasonic pulse. In some embodiments, the first and second areas are tiled to minimize overlap or gaps between areas of irradiated tissue. In some embodiments, the transducer may be used in a "gliding mode," where the transducer is moved in a continuous fashion. In some embodiments, the single ultrasonic pulse consists of multiple frequencies. The frequencies may be applied simultaneously or as a series of short pulses. Using a broad-area transducer (e.g., producing an ultrasonic beam larger than 4 mm wide) it may take approximately 10 to 30 minutes to treat a leg, and approximately 30 to 60 seconds to treat a chin.

In a preferred embodiment, a treatment protocol includes one pulse every 6 or less seconds, each pulse duration being less than 100 ms. In a more preferable embodiment, a treatment protocol includes one pulse every 3 or less seconds, each pulse duration being less than 100 ms.

By allowing multiple hairs to be treated within a single treatment area, a broad-area irradiation device provides a distinct advantage over focused beam methods. However, there are problems, unique to broad-area transducers, that are addressed by various aspects of the embodiments described herein.

A first consideration is that the peak power of the transducer active element may be much higher as compared to other medical ultrasound devices. Broad-area transducers may be characterized as having an unfocused or weakly focused energy beam. As a result, the transmitted energy in an unfocused beam is distributed over a larger area than that of a focused beam. The intensity of the beam may be increased to achieve the desired exposure level in the hair follicles. Depending on the frequency and pulse duration used, the peak intensity energy required at the hair follicle to achieve hair removal may be between 150 and 1000 W/cm². Because the beam is collimated, this energy is also the output intensity required at the active element of the transducer (e.g., piezoelectric disk). In comparison, the highest power focused ultrasound transducers typically produce intensities up to 4 W/cm² at the active element and transducers used for physiotherapy and diagnostic application produce up to 0.2 and 5 W/cm², respectively. (C. R. Hill et al. *Physical Principles of Medical Ultrasonics*, $2^{nd}$ edition, John Wiley & Sons Ltd (2004).)

A second consideration is that an increase in ultrasonic power may produce more thermal energy, increasing the risk that the tissue being treated will be overheated or damaged. In some embodiments, cooling may be provided to prevent the tissue (e.g., epidermis tissue) from overheating. For example, the cooling may be provided by contacting a chilled surface to the skin tissue, commonly referred to as a "chill plate." Cooling may be applied before ("pre-cooling") or after ("post-cooling") the exposure or by some combination thereof. In some embodiments, the chill plate temperature may be set between 5 and 30 degrees Celsius and preferably between 5 and 20 degrees Celsius. In some embodiments, the cooling period is 0.5 seconds or longer. In general, the cooling period depends on multiple factors including the chill plate temperature, thermal conductance of the chill plate, and the fluence of the exposure.

The transducer should also include a mass acting as an impedance-matching element which matches the acoustic impedance of the transducer active element (typically a piezoelectric disk) to the impedance of the skin. Using a mass to match the acoustic impedance between the media reduces reflected energy and improves the efficiency of the transmission.

FIG. 1 depicts a schematic diagram of an ultrasonic transducer device including a transducer housing 106, a piezo element 102, and impedance-matching element 104. In some embodiments the mass and materials of impedance-matching element 104 are selected to match the impedance of the piezo 102 to the tissue 120 being treated. The tissue contains one or more hair shafts 124 and one or more hair bulbs 122. In some embodiments, the ultrasonic transducer device is capable of producing a substantially collimated energy beam 110. In some embodiments, what is meant by producing a substantially collimated energy beam is that the beam does not vary by more than 20% over a distance of at least 5 mm from the surface of the skin tissue to a treatment plane. In some embodiments, what is meant by producing a substantially collimated energy beam is that the beam does not vary by more than 10% over a distance of at least 5 mm from the surface of the skin tissue to a treatment plane. In other embodiments, what is meant by producing a substantially collimated energy beam is that the beam does not vary by more than 5% over a distance of at least 5 mm from the surface of the skin tissue to a treatment plane.

In some embodiments, a chill plate is used to cool the tissue 120 being treated. In some embodiments the impedance-matching element 104 also acts as a chill plate, reducing the complexity of the device. A well-designed impedance-matching chill plate should posses the following properties: (1) one or more layers of material whose thicknesses and acoustic impedances are chosen to maximize the transmission of acoustic energy into the skin; and (2) good thermal conductivity in order to extract heat from the tissue for efficient cooling.

In a preferred embodiment, the impedance-matching chill plate consists of one or more layers whose thickness and acoustic impedances are chosen such that at least 50% of the ultrasonic energy produced by the piezo 102 is transmitted to the skin tissue 120. In some embodiments, the impedance-matching chill plate consists of one or more layers whose thickness and acoustic impedances are chosen such that at least 75% of the ultrasonic energy produced by the piezo 102 is transmitted to the skin tissue 120.

Materials suitable for a chill plate include, for example, aluminum, copper, brass, glass, fused silica, sapphire, and epoxy. A material with thermal conductivity comparable to or better than one of these materials is preferred. In some embodiments the thermal conductivity is equal to or greater than 1 W/m K. In some embodiments, the impedance-matching chill plate may be mounted to a temperature-regulated housing that acts as a heat sink.

A third consideration when using a transducer producing a broad, collimated beam is that a uniform energy distribution is produced in the hair follicles being irradiated. When using a broad, collimated beam, the energy profile is typically irregular in portions of the beam close to the source. This portion of the beam is also referred to as the near-field. While the beam area and average energy intensity across the beam are relatively constant through the near-field, the energy profile may exhibit strong oscillations due to interference effects. As a result, there will be zones of relatively low intensity and zones of relatively high intensity. Hairs located in low-intensity zones may be under-treated and their ability to regenerate unaffected.

Figure 2:
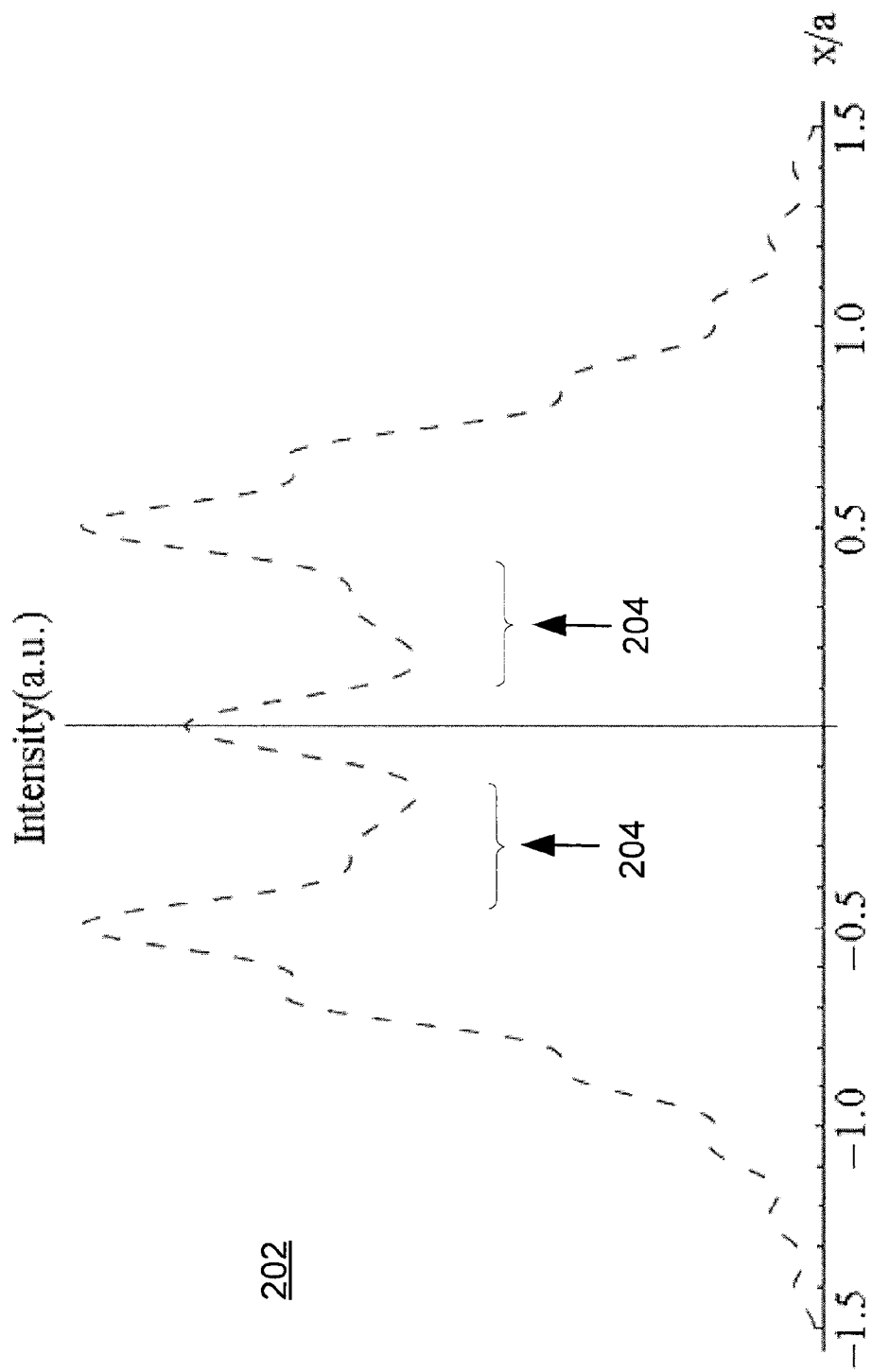
FIG. 2 depicts an intensity profile of a 10 MHz source 2 mm from a 2-mm-wide aperture.

FIG. 2 depicts an example of a near-field intensity profile 202 produced using a 10 MHz source and a 2-mm-wide aperture. The aperture half-width (a) may be defined as the aperture width/2. The profile is calculated at a distance of 2 mm from the aperture plane. As shown in FIG. 2, there are multiple zones of low intensity 204 approximately 0.5 mm wide. The width of a hair structure is typically less than 0.25 mm and the length of the bulb and bulge of a hair follicle are about 0.5 mm or less. A transducer with an intensity profile similar to the profile depicted in FIG. 2 may under-treat hairs located in low-energy zones of the beam.

The near-field may be defined as the region of the beam where the distance (z) from the active element is less than the Rayleigh range ($z_R$). The Rayleigh range is defined by the area (A) of the clear aperture of the transducer and the wavelength of the beam ($\lambda$) according to the equation:

$$Z_R = A/\lambda. \quad \text{(Equation 1)}$$

For example, for a 0.5-cm² aperture and 10 MHz ultrasound frequency, the near-field would extend to 33 cm—well beyond the face of the transducer. Therefore, simply placing the hair follicle (target) in the far-field of the transducer is not a practical solution. The following section discusses a number of embodiments directed toward eliminating or reducing the magnitude of these oscillations.

2. Aperture Size for Optimizing a Beam's Intensity Profile

There are a number of potential sources of near-field interference effects. In particular, the edges of a transducer's clear aperture produce edge waves that interfere with the wave transmitted geometrically through the clear aperture. This effect may create the ripples observed in the profile shown in FIG. 2. In practice, the clear aperture of the transducer may be determined, at least in part, by the aperture of the active area of the active element or by some other limiting aperture of the transducer device that defines the beam size, such as the housing or the impedance-matching element.

Reducing the amplitude and width of the ripples is desirable when the beam is used for hair removal. In one embodiment, the amplitude and width of the ripples may be reduced by increasing the width of the clear aperture of the transducer. The number of large scale ripples in the near-field may correlate to the Fresnel number (N), which is defined by the wavelength ($\lambda$), aperture half-width (or radius) (a), and distance from the aperture (z) by:

$$N = a^2/\lambda z. \quad \text{(Equation 2)}$$

Since the number of ripples increases with the square of the aperture radius (a), the width of the ripples will decrease linearly with increasing aperture size.

Figure 3:
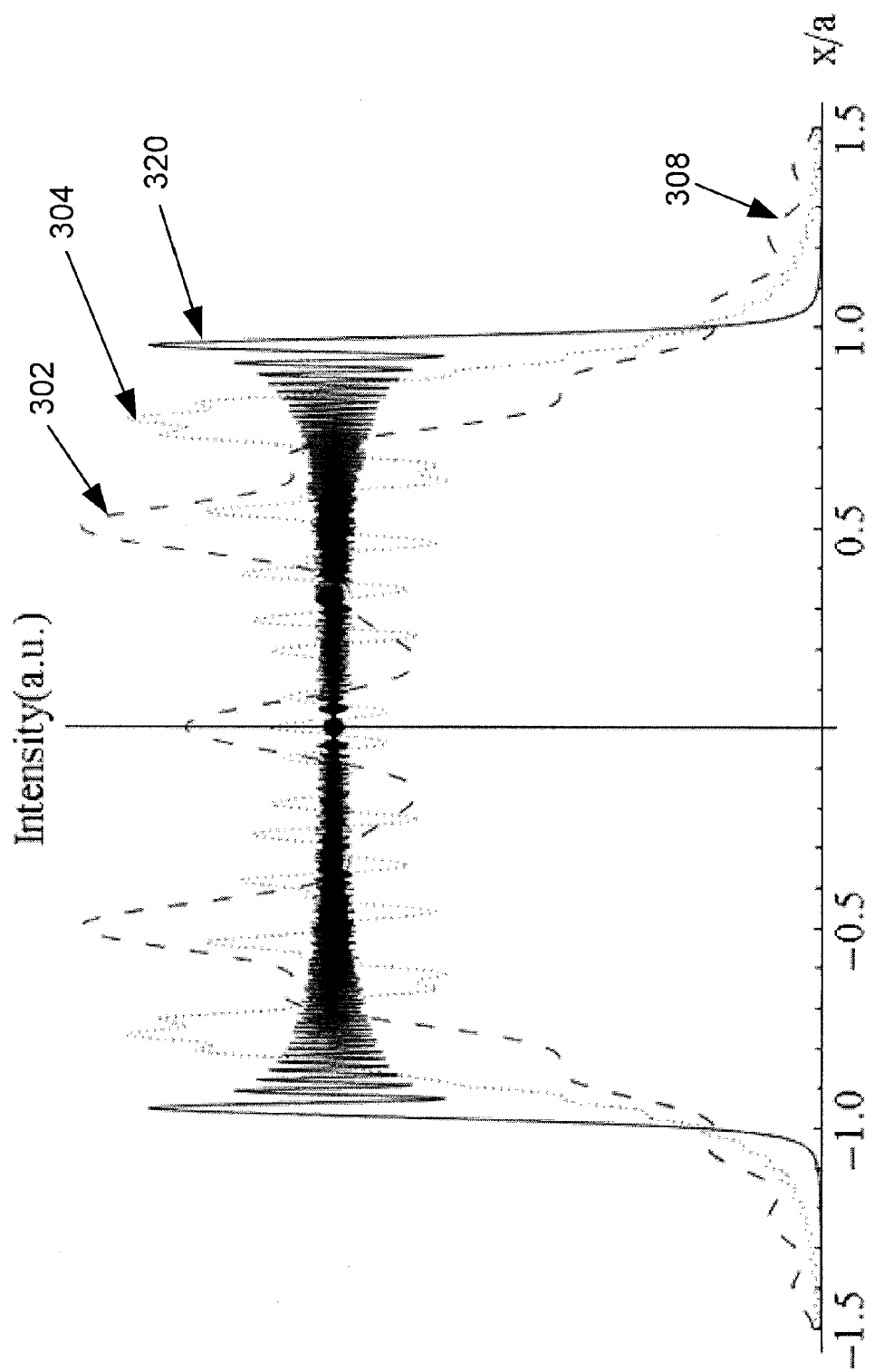
FIG. 3 depicts intensity profiles for a 10 MHz source 2 mm from apertures with widths of 2, 4, and 20 mm.

FIG. 3 depicts a plot of intensity profiles 302, 304, and 320 for aperture widths of 2, 4, and 20 mm, respectively. The intensity profiles are normalized as x/a, where x is the radial distance from the center of the aperture and the half-width (radius) of the aperture is a. As shown in FIG. 3, the amplitude of the ripples, especially in the central portion of the beam, is reduced dramatically as the width of the aperture is increased. Furthermore, as the aperture is increased, the spatial frequency increases, reducing the width of the "holes" in the intensity profile.

For most medical applications, the damage to the targeted tissue—and therefore the efficacy of the treatment—increases monotonically with the intensity of the applied radiation. Consequently, the optimum intensity is generally the maximum intensity that may be used without exceeding a threshold level that produces adverse side effects. A preferred intensity profile is a top-hat shape (for which the intensity is substantially constant) because the intensity may be set to an optimum value across the entire beam cross-section and treatment plane.

Figure 4:
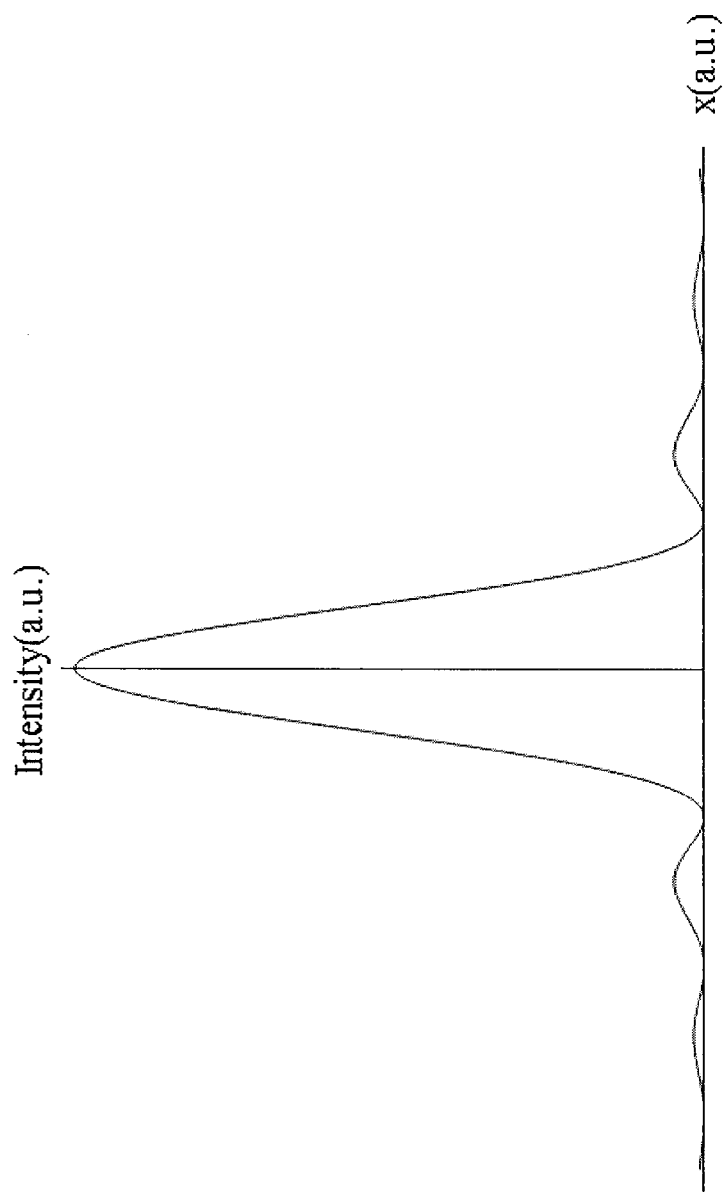
FIG. 4 depicts an intensity profile for a focused beam.

As seen in FIG. 3, another benefit of using a larger aperture for the ultrasound transducer is that the intensity profile approaches the ideal top-hat shape. Less energy is wasted in low-intensity tails 308, as observed at x/a>1 for the smaller aperture size, and the central portion of the beam approaches a constant intensity except at the edges. The high intensity at the edges may be attenuated using apodization (see, e.g., FIG. 10). Compare the intensity profiles of FIGS. 3 and 10 with that of a focused device, as shown in FIG. 4. A focused device may have an intensity profile close to the focal plane characterized by the well-known Airy pattern. As shown in FIG. 4, the intensity changes dramatically across the beam profile and, therefore, only a small fraction of the beam (e.g., a narrow region at the peak) may be set to the optimum intensity. In general, the beam profile will approach the Airy pattern for Fresnel numbers<0.5.

Figure 5:
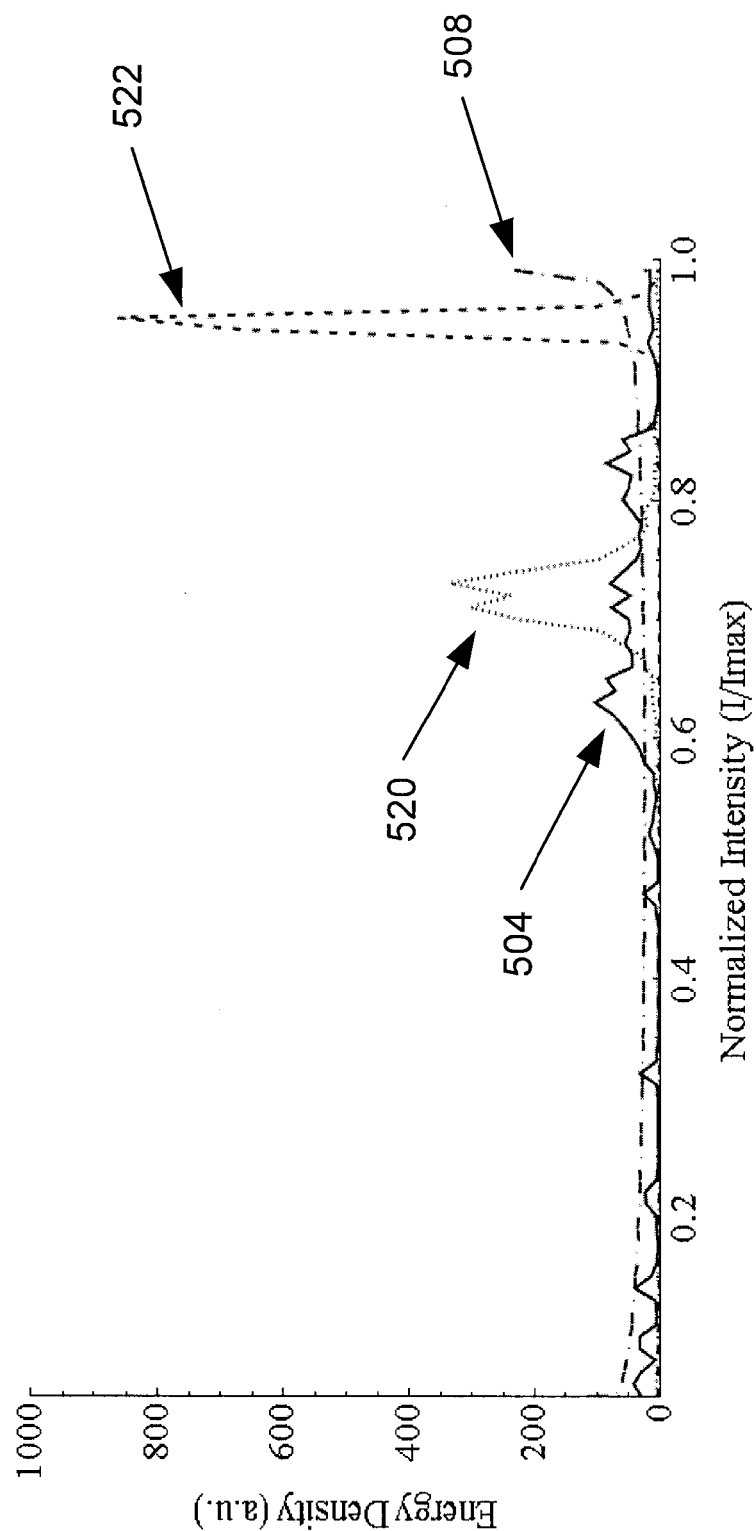
FIG. 5 depicts a comparison of normalized intensity distributions at 10 MHz.
Figure 10:
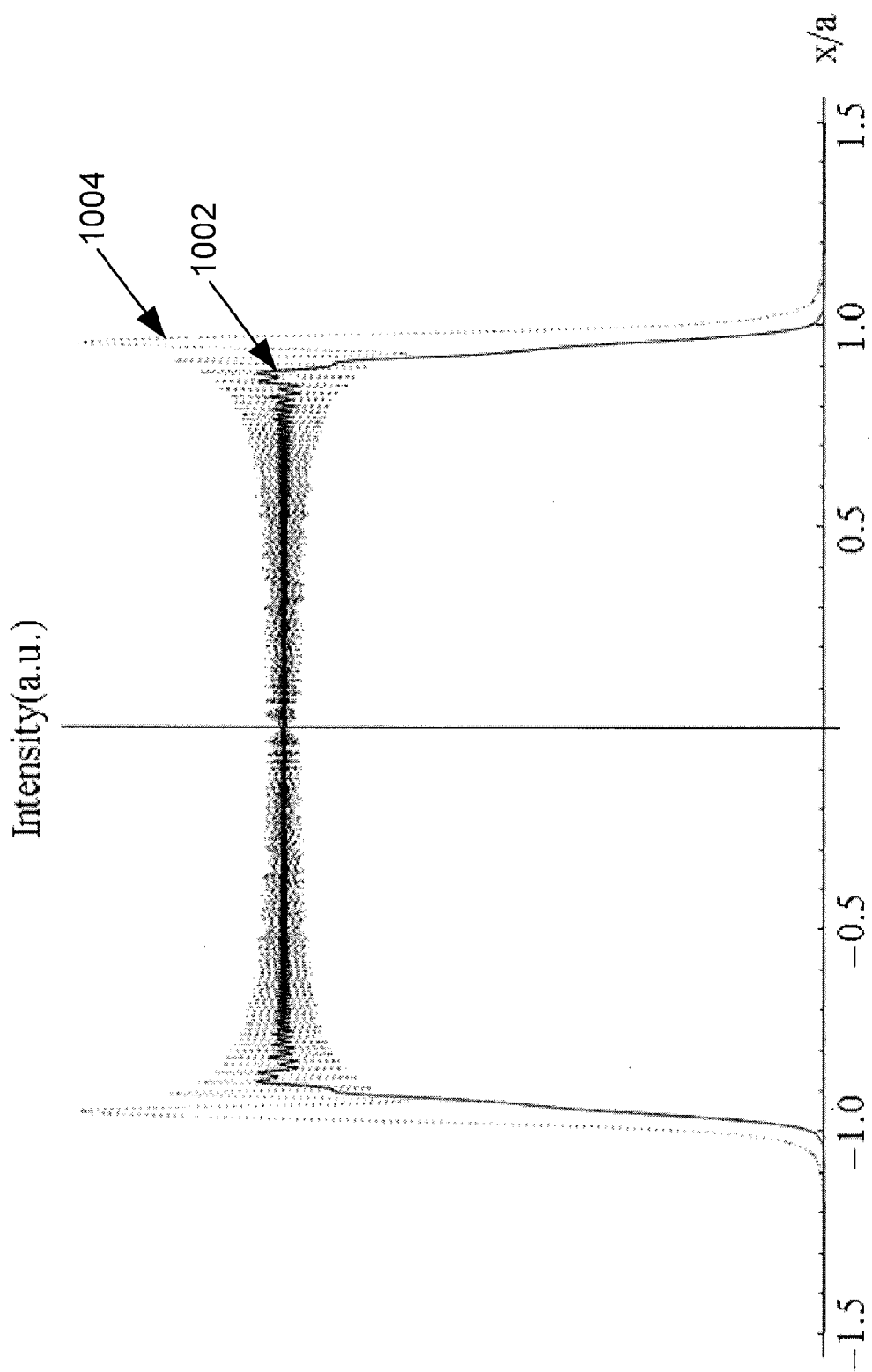
FIG. 10 depicts an intensity profile with and without apodization.

FIG. 5 compares the energy density versus normalized intensity for four ultrasonic beams, where the normalized intensity is the intensity divided by the maximum intensity $I_{max}$. Intensity distribution 504 represents the normalized intensity of a collimated beam, 2 mm from a 4-mm-wide aperture. The intensity distribution 504 may correspond to the intensity profile 304, as shown in FIG. 3. Intensity distribution 520 represents the normalized intensity of a collimated beam, 2 mm from a 20-mm-wide aperture. The intensity distribution 520 may correspond to the intensity profile 320, as shown in FIG. 3. Intensity distribution 522 represents the normalized intensity of a collimated beam, 2 mm from a 20-mm-wide, apodized aperture. The intensity distribution 522 may correspond to the intensity profile 1002, as shown in FIG. 10. Intensity distribution 508 represents the normalized intensity of a focused beam close to the focal plane. The intensity distribution 508 may correspond to a focused intensity profile, such as the Airy pattern shown in FIG. 4.

As shown in FIG. 5, a narrower intensity distribution may be achieved by locating the treatment plane in the near-field of a wide limiting aperture (i.e., at high Fresnel number). For a 4-mm-wide aperture, the intensity distribution 504 is concentrated between 65 and 85% of the maximum intensity. For a 20-mm-wide aperture, the intensity distribution 520 is narrower and is concentrated between 70 and 75% of the maximum intensity. By adding apodization to a 20 mm aperture, as shown in intensity profile 1002 (FIG. 10 below), the intensity distribution 522 is further narrowed to 94 to 96% of the maximum intensity. In comparison, the intensity distribution 508 for the focused beam is poorly concentrated and spans, relatively evenly, from 5 to 100%. In fact, the shape of the intensity profile for a focused beam is independent of the beam size. Therefore, the intensity distribution 508 cannot be made narrower by simply adjusting the size of the beam.

As described above, it is desirable to produce a beam that has a top-hat shape and to minimize the amplitude and maximize the spatial frequency of any ripples in the profile. In some embodiments, the quality of the beam's intensity profile scales with the Fresnel number (N) defined in Equation 2. For the 2-, 4-, and 20-mm-wide aperture intensity profiles (302, 304, 320) shown in FIG. 3, the corresponding Fresnel numbers (N) are 3, 13, and 333, respectively. For the purpose of hair removal, a Fresnel number greater than 3 and more preferably greater than 10 is desirable, calculated using distance (z) as the distance from the clear aperture of the device to the target tissue (e.g., depth of the hair follicles). The distance (z) may also be expressed as the distance from the limiting aperture (e.g., face of transmitting piezo) to a treatment plane. For hair removal applications, the treatment plane is the average depth of the hair follicles in the skin tissue.

3. Aperture Shape for Optimizing a Beam's Intensity Profile

The intensity profiles shown in, for example, FIGS. 2 and 3 were calculated for a 1-dimensional slit. While the improvements in beam quality with Fresnel number noted above also apply generally to 2-dimensional apertures of arbitrary shape, there are additional considerations that arise when considering 2-dimensional apertures. For a rectangular aperture, the acoustic field will simply be the convolution of the fields produced by two 1-dimensional slits rotated by 90 degrees. Therefore, the intensity profiles produced along cross-sections parallel to the edges of the aperture will be similar to those shown in FIG. 2 and FIG. 3.

Figure 6A:
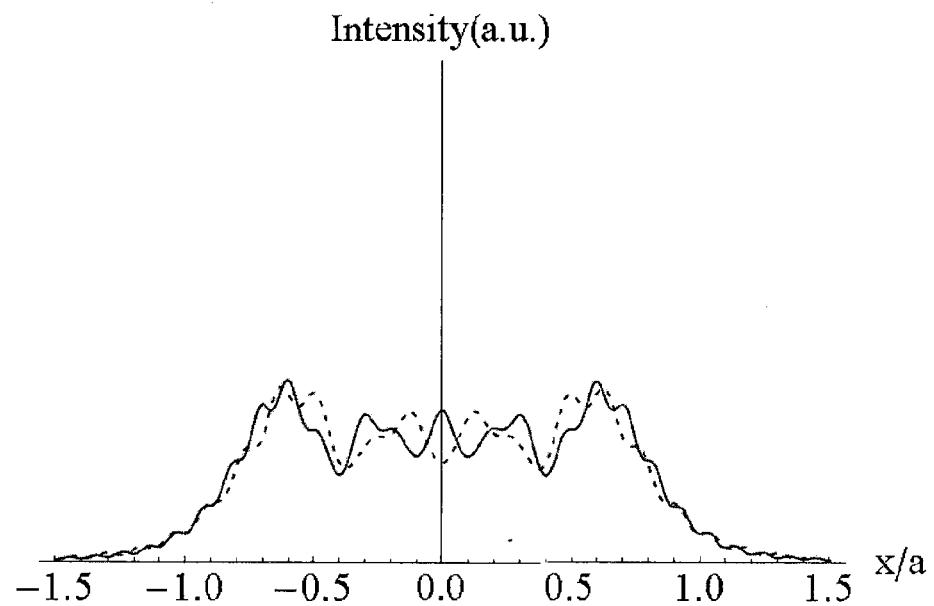
FIG. 6a depicts an intensity profile for a 2-mm square aperture.
Figure 6B:
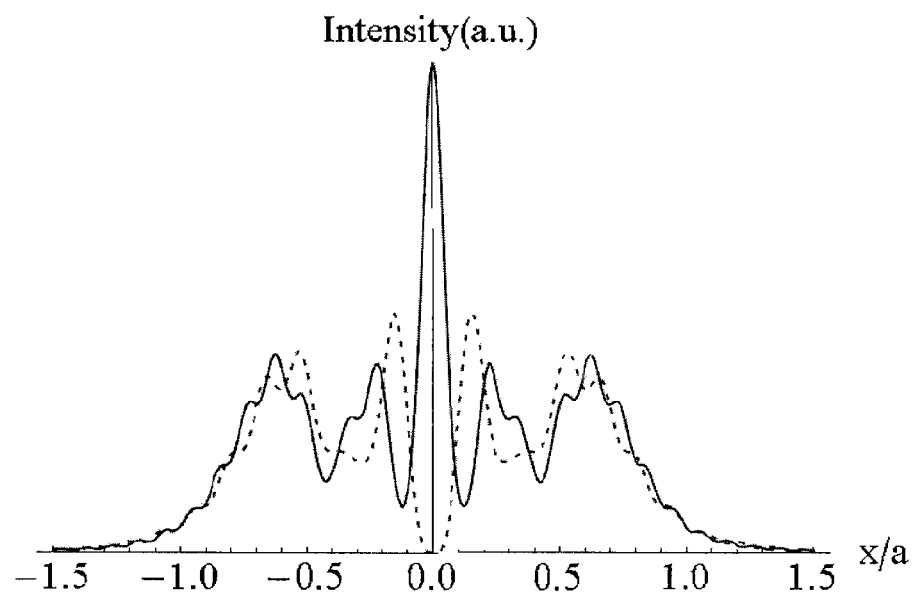
FIG. 6b depicts an intensity profile for a 2-mm circular aperture.

However, for a non-rectangular aperture, additional ripples in the profile may be observed. For example, this effect may be observed for a circular aperture which may have a strong spike or hole in the intensity profile, on-axis with the center of the transducer. FIGS. 6a and 6b show a comparison of intensity profiles for 2-mm-wide square and circular apertures, respectively. The on-axis intensity for the square aperture is relatively even, while for the circle it oscillates between 0 and about 4 times the average intensity. If a hair follicle were located in the hole of the circular aperture, it would be undertreated. Furthermore, the spike could also result in overtreatment or damage to the skin. In fact, the peak amplitude of the on-axis oscillation for a circular aperture (in the near-field) is independent of the Fresnel number and therefore cannot be reduced by changing the nominal size of the clear aperture.

In general, there are 2 advantages for using a rectangular (or square) aperture for hair removal. First, it provides better on-axis beam quality with higher efficacy and less risk of overexposure. Second, with a rectangular aperture it is easier to treat an extended area at a fixed dosimetry since the area may be neatly tiled into rows and columns without gaps or overlap between treatment spots.

Figure 7A:
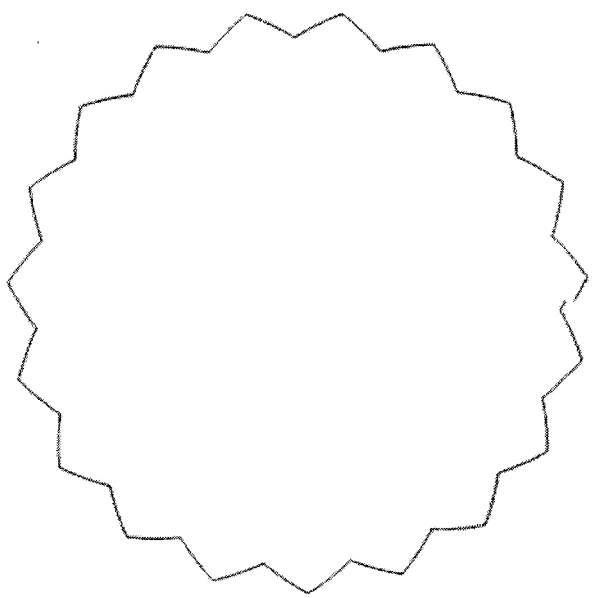
FIGS. 7a and 7b depict examples of rounded aperture shapes with irregular edges.
Figure 7B:
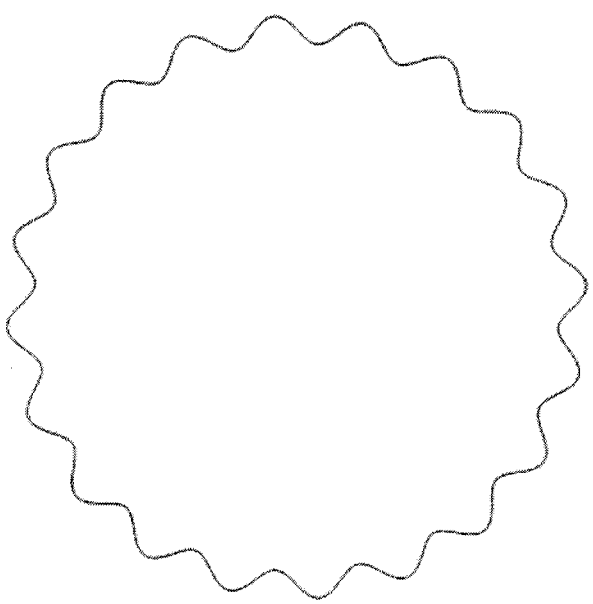

In practice, modest deviations from a circular shape would also improve the beam quality. Examples include an ellipse or round shape with irregular edges, as shown in FIG. 7a and FIG. 7b. In some embodiments, the aperture has a serrated, rippled, notched, or jagged edge profile.

4. An Apodized Aperture for Optimizing a Beam's Intensity Profile

As discussed above, a transducer design with a large Fresnel number may be used to produce a beam with an improved intensity profile. In some embodiments, an improved profile is a profile that approaches a top-hat-like shape and reduces the amplitude of the ripples across the center of the beam. However, as illustrated in FIG. 3, the improved intensity profile (at least in the near-field) still has peaks at the edges that are not attenuated by increasing the Fresnel number. For applications such as hair removal, it is desirable to produce a beam with a uniform intensity profile such that the intended dosimetry may be delivered across the entire beam. One method to reduce the edge effects is to soften or "apodize" the edges of the limiting aperture by eliminating the single-step discontinuity in the aperture transmission at the edge. For example, a multi-step or continuous transmission gradient may be used.

Figure 8:
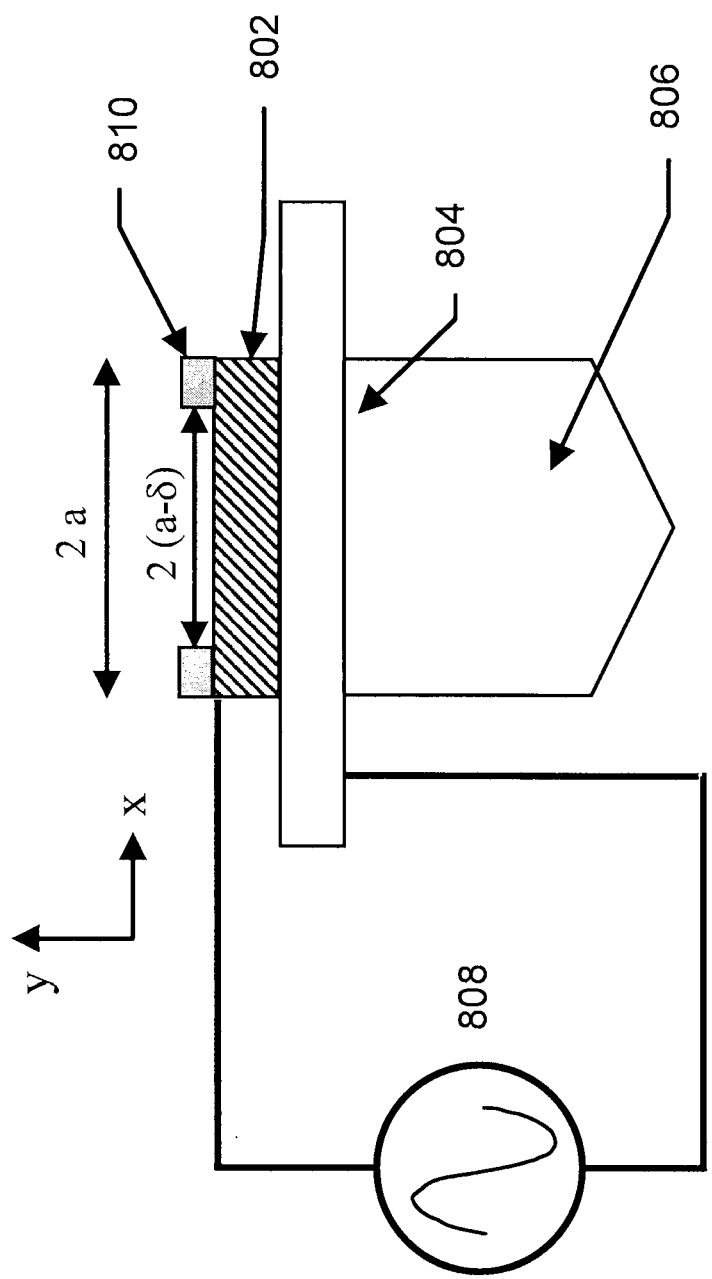
FIG. 8 depicts an air-backed piezo transducer with an apodizing annulus.

As an example, FIG. 8 depicts an embodiment including a transducer for which the active element is an air-backed piezo disk 802 coupled to an impedance-matching plate 804 to produce an acoustic beam 806. An apodizing annulus 810 is coupled to the piezo disk 802. In this embodiment the edges of the piezo disk 802 define the clear aperture of the device. An AC voltage element 808 is used to drive the piezo disk 802 in a piston mode such that it vibrates along the y-axis. As the piezo 802 vibrates, an acoustic wave is generated at the piezo-air interface. Due to the large acoustic impedance discontinuity at the air interface, acoustic waves are strongly reflected at the transition and propagate back through the impedance-matching plate 804. Without apodization, the reflection will be nearly 100% across the air interface of the piezo up to the edges.

Figure 9:
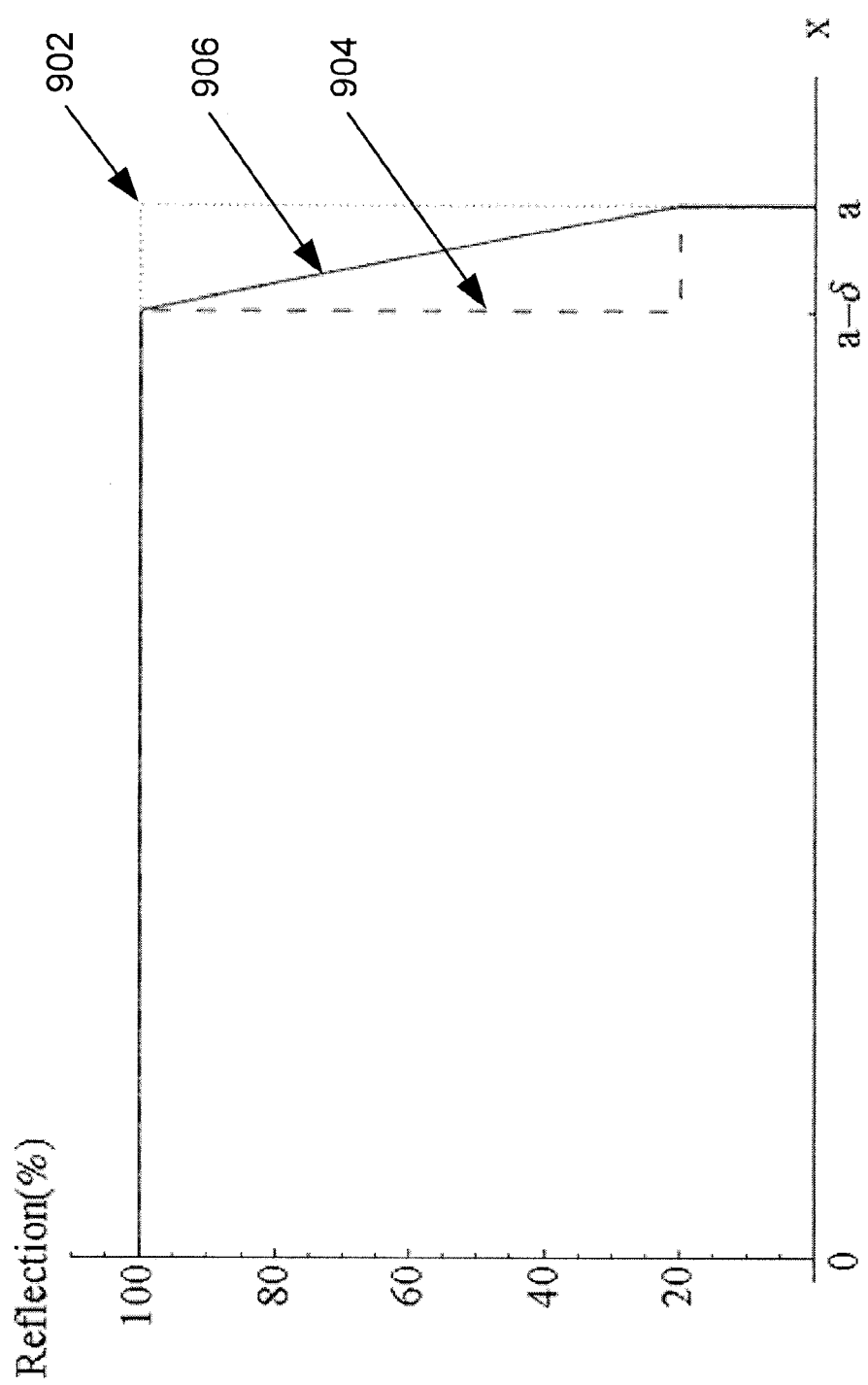
FIG. 9 depicts an example of reflection reduction using stepped and graded apodization.

As shown in FIG. 8, an apodizing annulus 810 may be added to reduce the reflection at the air interface by causing a stepped or graded reflection. FIGS. 9 and 10 illustrate exemplary effects created using a stepped or graded apodizing element. FIG. 9 depicts the reflected intensity across an air-piezo interface for a piezo with an aperture radius (a). The reflection profile 902 represents an air-piezo interface without apodization. The reflection profile 904 represents an air-piezo interface with a stepped apodization and the reflection profile 906 represents a graded apodization. In some embodiments, the stepped apodization is achieved using an annulus, as shown in FIG. 8. In some embodiments, the graded apodization is achieved using a tapered or variable impedance annulus.

FIG. 10 shows a comparison of the resulting intensity profiles without and with the graded apodization. The transducer in FIG. 10 is for a beam with a Fresnel number of 333 using a graded apodization similar to the reflection profile 906 in FIG. 9. In particular, the intensity profile 1002 is for a transducer with a graded apodization. The intensity profile 1004 is for a transducer with no apodization. The intensity profile 1002 demonstrates how apodization can be an effective means for eliminating the high-intensity peaks at the edges of near-field beam's intensity profile. Using apodization, even the amplitude of the ripples towards the center of the beam is reduced.

Whatever the physical origin of the effective aperture (the active element, the matching plate, etc.), the general principle of apodizing the edges to eliminate edge effects may be applied. Generally speaking, the apodization has the property that it modifies the amplitude and or the phase of the wave at the aperture edges in a way to eliminate a single-step discontinuity in transmission.

For example, in some embodiments, an apodizing annulus may be constructed using layers of materials, each layer having a slightly higher acoustic impedance. By minimizing the change in acoustic impedance from piezo to the air interface, the reflected waves would be reduced, resulting in a more uniform intensity profile. In other embodiments, the apodizing annulus could be placed on the opposite side of the piezo to attenuate the edges of the transmitted beam's intensity profile. In other embodiments, portions of the acoustic beam could be reflected back to the active element to produce a more uniform intensity profile. Other techniques known in the art could also be used to apodize the edges of the transmitted beam. For example, the irregular aperture edges shown in FIG. 7a and FIG. 7b provide a form of apodization.

6. Using Frequency Modulation to Optimize a Beam's Intensity Profile

As described above, the near-field of an acoustic beam is susceptible to interference from secondary waves that may be caused by abrupt transitions in the transducer medium. For example, the edges of the aperture or an air-transducer interface can cause ripples in a beam's intensity profile. Different aspects of the embodiments described above can be used to minimize some of these interference effects.

However, imperfections in the design or construction of the transducer may create additional transitions within in the transducer materials (e.g., piezo element, impedance-matching element, chill plate). For example, defects in the transducer materials or bond lines can produce scattering. Also, small acoustic impedance mismatches at material interfaces may result in reflections that interfere with the primary beam. Interference from these secondary waves may result in ripples or hot spots in the near-field intensity profile. In some cases, a secondary wave that contains 1% of the total beam power can produce ripples in the near-field intensity that have a peak-to-peak amplitude equal to 40% of the average intensity. As previously discussed, inconsistency in the beam intensity may result in underexposure of hairs located in zones of low intensity, rendering the irradiation treatment ineffective for at least some of the hairs.

In some cases, it may not be practical, or even possible, to reduce such variations in the intensity profile using different aspects of the embodiments discussed above. Therefore, some embodiments may also include the ability to modulate the frequency of the device to reduce or eliminate variations in the effective intensity profile of the near-field transducer beam.

In general, the locations of the maxima and minima in an interference pattern depend on the frequency being transmitted. Further, it is possible to shift areas of low intensity by modifying the frequency. Therefore, zones of low intensity at a first frequency may be compensated for by transmitting a second beam using a second, different frequency. If the frequency is modulated at a rate that is faster than the thermal relaxation rate of the targeted tissue, the tissue will integrate the two intensity profiles during its thermal relaxation period. In some embodiments, the frequency is modulated at a rate that is greater than 0.25% of the average frequency per 100 milliseconds.

In some embodiments, the frequency modulation can be used to produce an effectively homogenous intensity distribution resulting in a smooth temperature profile across the hair follicles within the transducer beam. In such a case, all of the hair follicles within the treatment area may receive an effective irradiation treatment without overexposure or underexposure.

Figure 11:
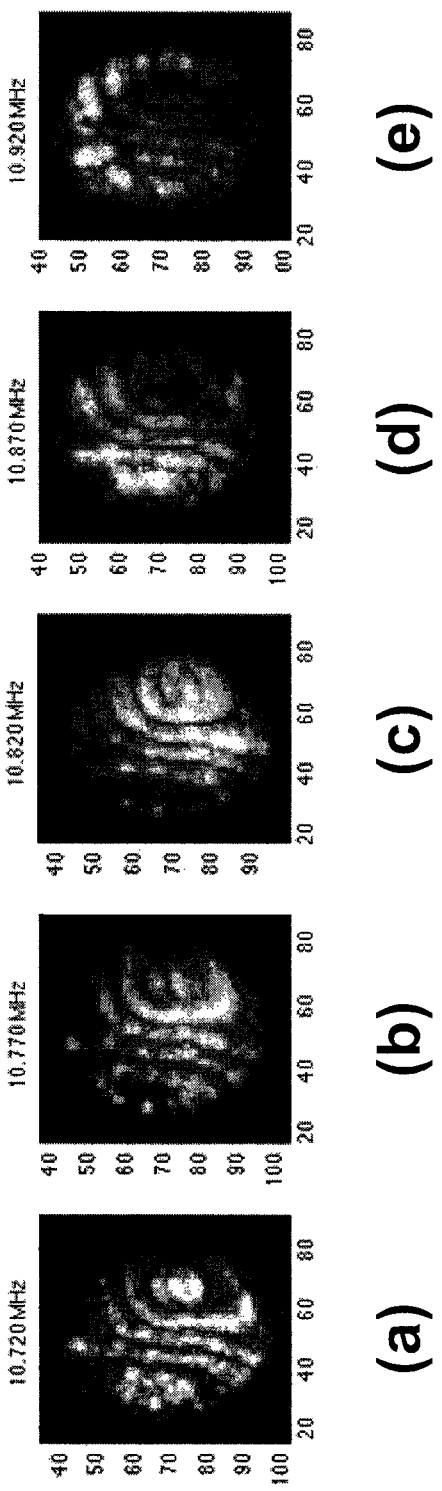
FIGS. 11a-e depict thermal images used to map a beam's transverse intensity profile created using a 20-mm wide transducer operated at (a) 10.72, (b) 10.77, (c) 10.82, (d) 10.87, and (e) 10.92 MHz using a 3-mm thick piece of tissue mimicking material.

FIG. 11a depicts an example of a thermal profile generated by a 1-cm-radius transducer operated at 10.72 MHz. In this case, the intensity profile is mapped by recording the thermal image in a 3-mm-thick sample of absorbing tissue mimicking material ("TMM"). The thermal image of an irradiated TMM approximates the ultrasound intensity profile that could be expected in a hair removal operation. As shown by the darker portions in FIG. 11a, there are low intensity portions of the irradiating energy approximately 1-mm-wide. Human hairs are approximately 100 um in diameter and spaced about 1 mm apart in an epidermal tissue. Using the irradiation intensity profile as shown in FIG. 11a to administer a hair reduction treatment would result in a significant portion of hair being underexposed and, therefore, unaffected by the treatment.

FIGS. 11b-e depict thermal profiles recorded at frequencies of 10.77, 10.82, 10.87, 10.92 MHz, respectively. The figures illustrate that the fringe pattern shifts spatially with changes in the irradiation frequency. Combining the intensity profiles of multiple irradiations, each at different frequencies, results in an effective beam profile that is more uniform. The combined profile will tend to be smoother since the intensity maxima at one frequency tend to fill in the minima at another.

Figure 12:
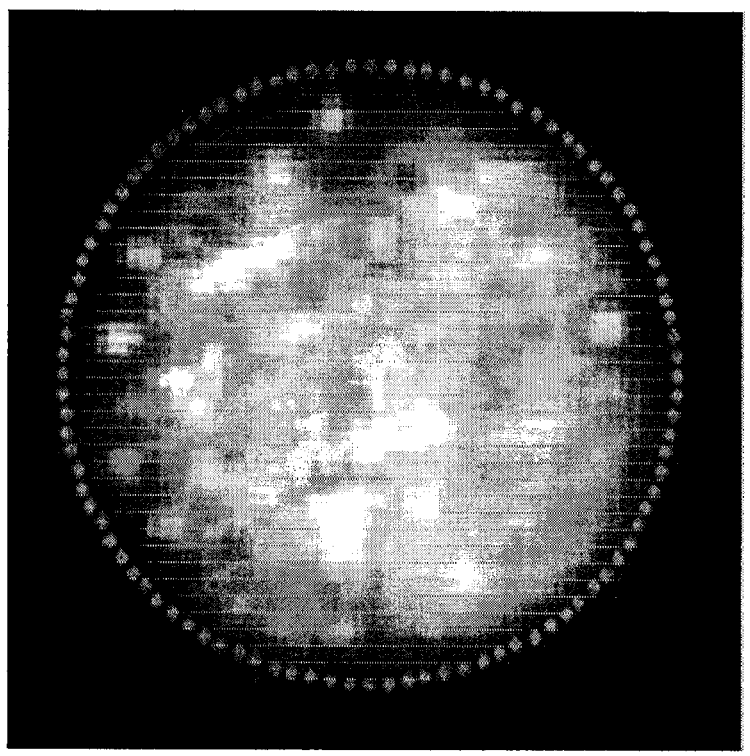
FIG. 12 depicts a superposition of thermal images used to map a beam's transverse intensity profile using a 20-mm-wide transducer operated at 10.72, 10.77, 10.82, 10.87, and 10.92 MHz for pulse durations of 5, 8, 5, 8, and 4 ms, respectively.

FIG. 12 shows an effective beam profile calculated by averaging the frequencies 10.72, 10.77, 10.82, 10.87, and 10.92 MHz using a weighting factor of 5:8:5:8:4, respectively. In practice, the multiple irradiations could be administered at each frequency for a pulse duration according to the weighting factor. In one embodiment, the frequencies 10.72, 10.77, 10.82, 10.87, and 10.92 MHz are each administered at a pulse time of 5:8:5:8:4 milliseconds, respectively. As indicated by the reduced low-intensity zones in FIG. 12, the homogeneity of the combined exposure has improved significantly. Therefore, the estimated efficacy of a hair reduction treatment using frequency modulation would be improved relative to a single frequency treatment.

FIGS. 13a and 13b compare calculated combined frequency profiles with a corresponding measured (actual) frequency-modulated profile as applied to a TMM. FIG. 13a depicts a calculated and measured thermal profile using two frequencies with a 2:1 weighting. FIG. 13b depicts a calculated and measured thermal profile using six frequencies with 1:1:2:7:4:3 weighting. As illustrated in FIGS. 13a and 13b, the experimental results agree reasonably well with the calculation.

In some embodiments, the weighting may be realized by modulating the frequency and controlling the dwell time at each frequency. In some embodiments, the frequency may be swept though one or more ranges of frequencies over a treatment time. In some embodiments, the one or more pulses may be separated by a pause to allow the thermal energy in the tissue to dissipate. In some embodiments, a modulation of the drive frequency of 1% produces a significant improvement in the homogeneity of the exposure. Therefore, in a preferred embodiment, the frequency range of the drive signal should be equal to or greater than 0.25% of the average drive frequency. In a more preferred embodiment, the frequency range of the drive signal should be equal to or greater than 1% of the average drive frequency.

Figure 14A:
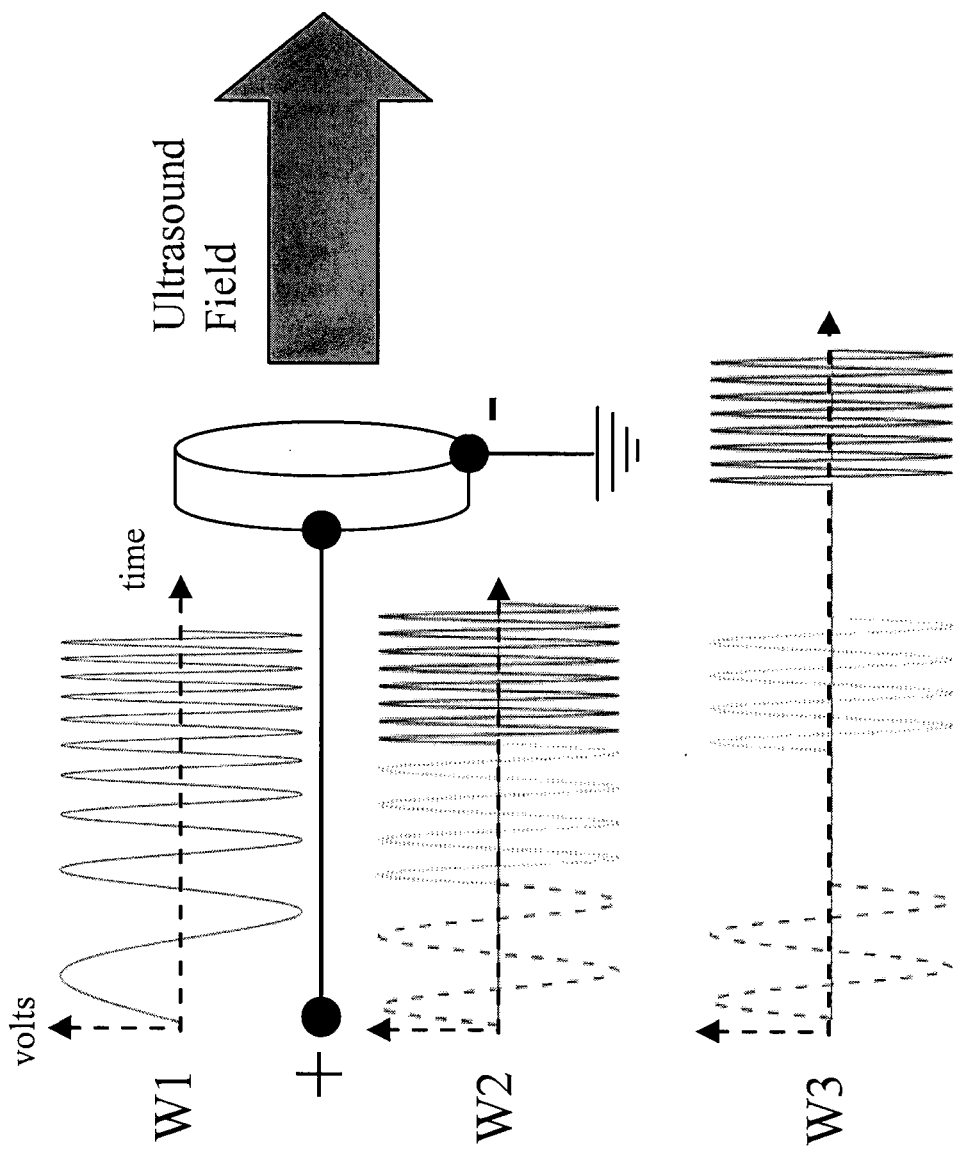
FIG. 14a depicts a single-element transducer with input waveform to positive electrode.
Figure 14B:
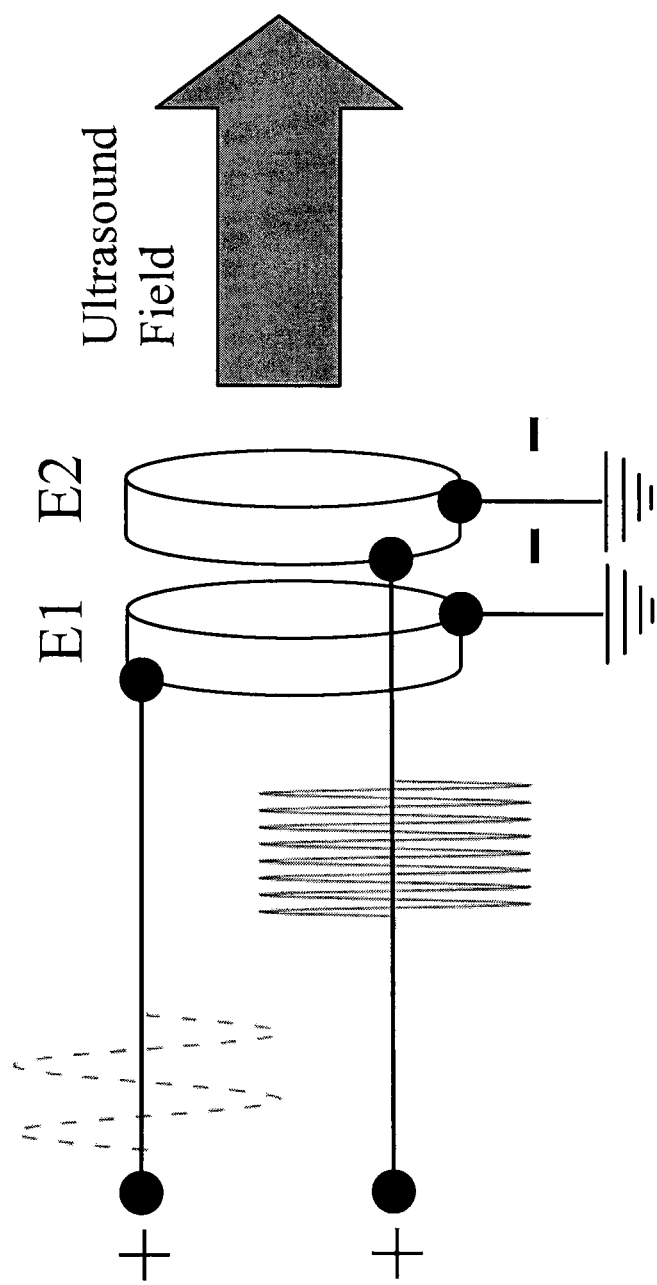
FIG. 14b depicts a multi-element transducer with each element being driven with a different energy pulse.

FIGS. 14a and 14b depict exemplary embodiments using frequency modulation. FIG. 14a shows a single-element device driven with a frequency-modulated waveform. The waveform may consist of multiple discrete frequency steps, a continuous frequency sweep, or some combination thereof. The frequency steps or sweep may be realized within a single pulse (as shown in waveforms W1 and W2) or a series of pulses. For example, W3 shows a series of 3 single-frequency pulses each having a different frequency. In this case, the improvement in the homogeneity of the exposure is due to the cumulative effect of multiple pulses. FIG. 14b depicts another embodiment using multiple elements, each element driven sequentially at different frequencies. The waveforms of the devices could also overlap in time and each waveform could consist of multiple discrete frequency steps, a continuous frequency sweep, or some combination thereof. In addition, a variety of 3-dimensional geometric arrangements of the elements can be envisioned that would overlap the beams from each element on the target.

While the discussion above has focused on the spatial variation of the field in the transverse direction, the field will also vary rapidly with longitudinal distance from the transducer. A calculation of the field intensity for an exemplary 1-cm-radius transducer driven at 10 MHz is shown in FIG. 15.

Figure 15:
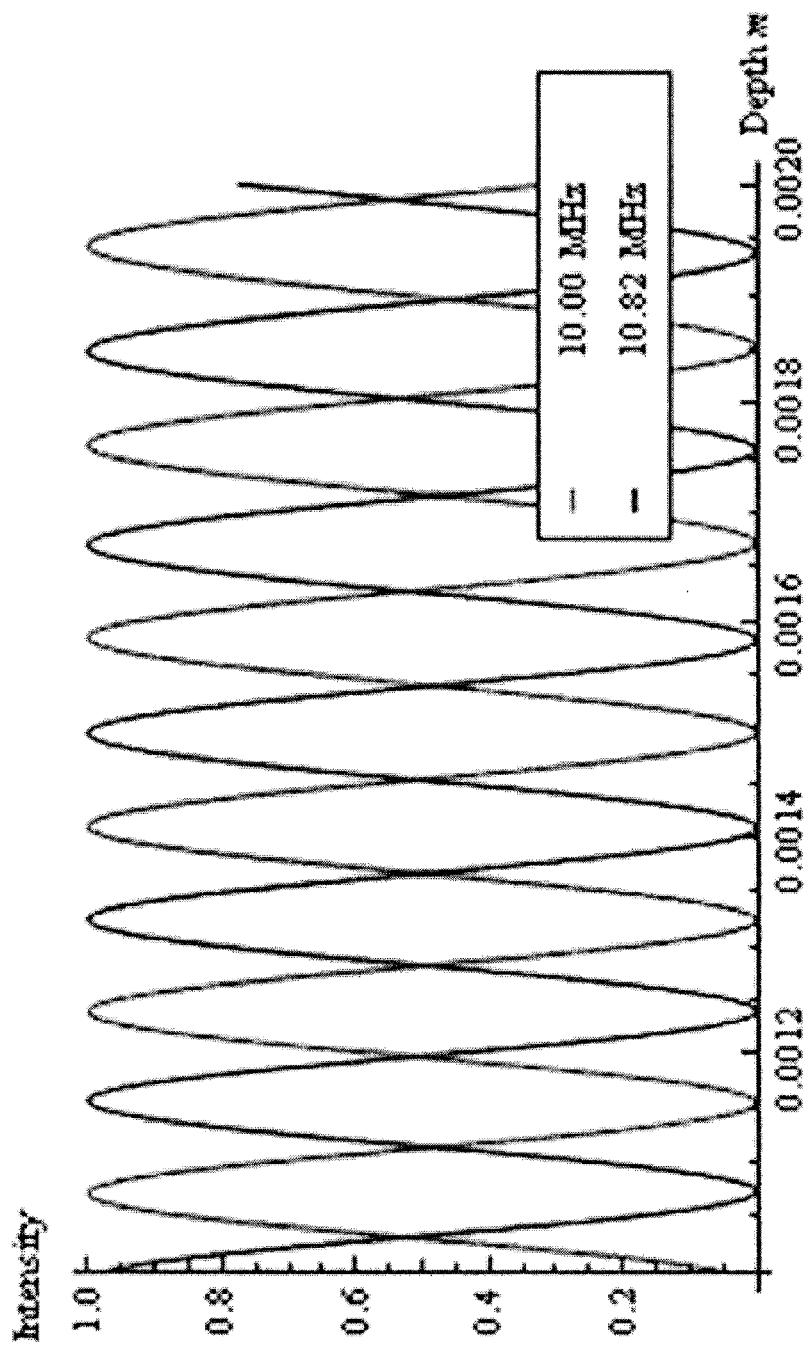
FIG. 15 depicts an exemplary longitudinal energy distribution.

As shown in FIG. 15, the intensity oscillates with a spatial period of about 200 um. Therefore, a target whose size scale in the longitudinal direction is on the order of 100 um might avoid exposure if the target were located close to a minimum in the longitudinal intensity profile. Typically, hair follicles are approximately 100 um in the longitudinal direction and their depth relative to the skin surface may vary by several 100 um. Therefore, exposure by a single frequency may not be effective since it will not affect the growth of hairs whose bulbs or follicles are located close to intensity minima. However, as was observed for the profiles in the transverse plane, the longitudinal intensity profile can also be shifted spatially by adjusting the drive frequency. FIG. 15 shows that shifting the frequency to 10.085 MHz results in an intensity profile shifted by half a spatial period with respect to 10.0 MHz. Therefore, the same concepts of frequency modulation and device design discussed above in relation to the exposure in the transverse plane, may also be employed to improve the efficacy in cases where the target size is comparable to or smaller than the spatial period of the intensity in the longitudinal direction.

7. Techniques for Imaging a Transmitted Beam without Affecting Intensity Profile In some cases, practical requirements or other physical constraints require the device to separate the transducer from the target by some distance. If the beam traverses this distance by simple free-space propagation then, according to Equation 2, the Fresnel number would decrease and therefore the beam quality would deteriorate. However, this limitation may be easily overcome by imaging the near-field intensity profile to a distant plane using acoustic lenses or mirrors. For example, if an acoustic lens of focal length (f) is placed a distance s1 from the near-field intensity profile, the near-field image will be reproduced at a distance equal to s2 on the opposite site of the lens. The parameters f, s1, and s2 are related by:

$$\frac{1}{f} = \frac{1}{s1} + \frac{1}{s2}.$$  (Equation 3)

Figure 16:
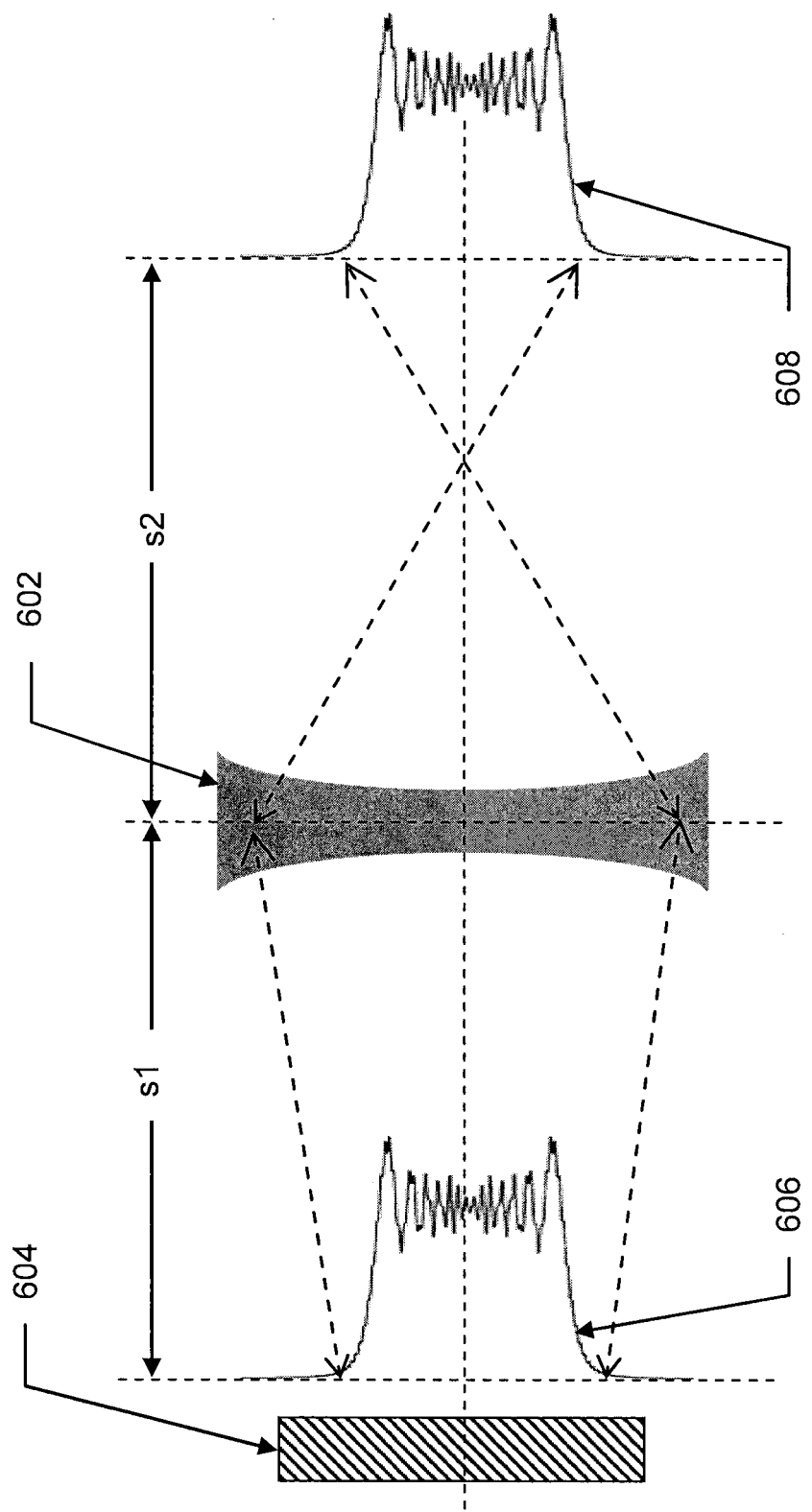
FIG. 16 depicts an example of beam imaging.

FIG. 16 depicts an example of imaging a beam using an acoustic lens 602. Item 606 represents a near-field beam profile produced using transducer 604 located a distance s1 from the imaging lens 602. Item 608 represents an image of the near-field profile projected a distance (s2) from the imaging lens 602. In other embodiments, a combination of lenses and mirrors, placed at appropriate locations, may be used to image the near-field and achieve a desired magnification, working distance, or physical distance between the object and image.

8. Exemplary System Using an Ultrasonic Transducer

Figure 17:
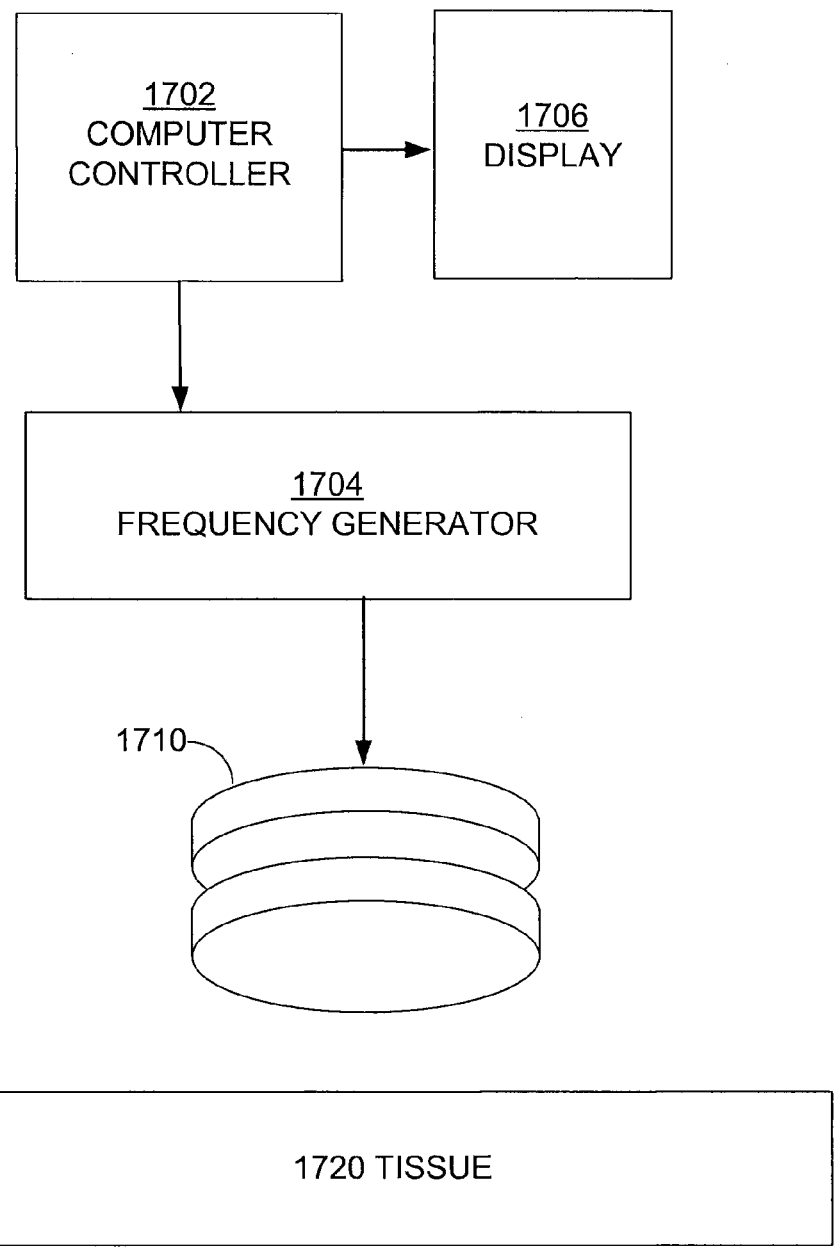
FIG. 17 depicts an exemplary system using an ultrasonic device.

FIG. 17 depicts an exemplary system 1700 using an ultrasonic transducer device for hair removal in a dermis tissue layer 1720. In one embodiment, one or more transducer elements 1710 are used to irradiate the tissue layer 1720 with an energy beam. In some embodiments, multiple transducer elements 1710 may be contained in one device housing. In some embodiments, more than one transducer elements 1710 may be stacked or aligned along a transmitting axis.

A frequency generator 1704 is used to produce the excitation voltage for the one or more transducer elements 1710. The frequency generator 1704 may be any waveform generation device suitable for delivering an ultrasonic frequency voltage to the one or more piezo elements used in the one or more transducer elements 1710. In some embodiments, more than one waveform-generation device is used as the frequency generator 1704. In some embodiments, the frequency generator 1704 may be controlled by a computer controller 1702. In some embodiments, the frequency generator 1704 includes an internal controller in addition to, or instead of, computer controller 1702. In a preferred embodiment, it is possible to set the frequency generator 1704 to more than one excitation frequency and more than one pulse time.

The computer controller 1702 may include one or more processors for executing computer-readable instructions. The computer-readable instructions allow the computer to control the frequency generator 1704 to produce one or more pulse frequencies at one or more pulse times. The computer controller may also include computer memory, such as read-only memory (ROM), random-access memory (RAM), and one or more non-volatile storage media drives for storing computer-readable instructions or programs. The computer controller may be equipped with a computer display 1706 or other visual read-out device.

It should be appreciated that the various features of the embodiments that have been described may be combined in various ways to produce numerous additional embodiments. Accordingly, the invention is not to be limited by those specific embodiments and methods described herein.

We claim:

1. A method of inhibiting hair growth in a skin tissue, the method comprising:
    placing a unitary ultrasonic transducer in contact with the skin tissue, the transducer having an acoustic aperture for producing a substantially collimated energy beam over a treatment area greater than 16 mm$^2$, wherein the substantially collimated energy beam is produced by a single transducer element, wherein the cross-sectional area of the substantially collimated energy beam does not vary by more than 20% over a distance of at least 5 mm from the surface of the skin tissue to a treatment plane, and wherein a chilled surface is in contact with the skin tissue, the tissue having a plurality of hair follicles within the treatment area; and
    generating a plurality of ultrasonic energy pulses, by supplying a drive frequency to the transducer, said pulses for heating the hair follicles, said pulses being generated with at least two different drive frequencies selected to reduce variations in the intensity profile across the treatment area.

2. The method of claim 1, wherein a combined pulse widths of all of the energy pulses total less than 100 ms.

3. The method if claim 1, wherein the intensity of the ultrasonic energy pulse at the transducer is greater than 150 W/cm2.

4. The method of claim 1, wherein the frequency of the ultrasonic energy pulses are between 5 and 20 MHz.

5. A method as recited in claim 1 wherein the variation between the two drive frequencies is at least 0.25% of the average drive frequency.

6. A method as recited in claim 1 wherein the variation between the two drive frequencies is at least 1.0% of the average drive frequency.

7. A method of inhibiting hair growth in a skin tissue, the method comprising:
    placing a unitary ultrasonic transducer in contact with the skin tissue, the skin tissue including a plurality of hair follicles, the transducer having a surface area greater than 1 cm$^2$ in contact with the skin tissue;
    generating a plurality of ultrasonic energy pulses, by driving the transducer with a drive frequency, said pulses for heating the hair follicles with a substantially collimated beam, wherein the substantially collimated beam is produced by a single transducer element of the unitary ultrasonic transducer, and wherein the cross-sectional area of the substantially collimated energy beam does not vary by more than 20% over a distance of at least 5 mm from the surface of the skin tissue to a treatment plane; and
    varying the drive frequency of the pulses to reduce variations in the intensity profile across the treatment area.

8. A method as recited in claim 7 wherein the difference between the highest drive frequency and the lowest drive frequency is at least 0.25% of the average drive frequency.

9. A method as recited in claim 7 wherein the difference between the highest drive frequency and the lowest drive frequency is at least 1.0% of the average drive frequency.

* * * * *